United States Patent [19]

Medina

[11] Patent Number: 5,690,123
[45] Date of Patent: Nov. 25, 1997

[54] METHOD OF ALTERING THE SHAPE OF THE CORNEA

[76] Inventor: Antonio Medina, P.O. Box 2355, Costa Mesa, Calif. 92628

[21] Appl. No.: 680,497

[22] Filed: Jul. 15, 1996

[51] Int. Cl.$^6$ .................................................. A61B 17/00
[52] U.S. Cl. .................................... 128/898; 606/166
[58] Field of Search .................... 606/166, 204.25, 606/1; 128/898

[56] References Cited

U.S. PATENT DOCUMENTS

| | | | |
|---|---|---|---|
| 3,074,407 | 1/1963 | Moon et al. | 606/166 |
| 4,417,579 | 11/1983 | Soloviev et al. | 606/166 |
| 4,619,259 | 10/1986 | Graybill et al. | 606/166 |
| 4,688,570 | 8/1987 | Kramer et al. | 606/166 |
| 4,744,362 | 5/1988 | Grundler | 606/166 |
| 5,108,412 | 4/1992 | Krumeich et al. | 606/166 |

FOREIGN PATENT DOCUMENTS

| | | | |
|---|---|---|---|
| 1068118 | 1/1984 | U.S.S.R. | 606/166 |

*Primary Examiner*—Michael H. Thaler

[57] ABSTRACT

A device is provided to plastically change the shape of the cornea by application of a vacuum. The device has elongated openings that are connected to a vacuum pump. By placing the device on the surface of the cornea and then applying a vacuum, a plastic deformation of the area of the cornea below the openings is achieved. The resulting effect is that the curvature and the refractive power of the cornea and the eye are changed. A flatter cornea reduces or corrects myopia or nearsightedness. Applications extend to correction of all refractive errors: myopia, hyperopia and astigmatism.

1 Claim, 6 Drawing Sheets

METHOD OF ALTERING THE SHAPE OF THE CORNEA

BACKGROUND OF THE INVENTION

This invention relates to improved means to correct refractive errors of the eye: myopia, hyperopia and astigmatism. Several attempts have been made to correct refractive errors by altering the shape of the cornea of the eye. A procedure called "orthokeratology" has been used for several decades with limited results. The procedure consists in prescribing a series of hard contact lenses over an extended period of time when the curvature of the lenses is progressively changed. The lenses in turn mold and change the curvature of the cornea.

Orthokeratology is a painful procedure because the lenses worn are a poor fit to the shape of the cornea since they must necessarily be of a curvature different than the cornea. Another problem encountered with this procedure is that unless lenses are worn regularly the curvature of the cornea reverts to its original value.

Surgical methods to alter the shape of the cornea have been proposed. Significantly two are currently in use: "radial keratotomy" and "photo-refractive keratectomy". Radial keratotomy is a procedure by which the cornea is cut in almost its full depth in a radial pattern. The cuts cause the cornea to flatten. Myopia is corrected with some success by radial keratotomy. Hyperopia cannot be corrected. Problems encountered with this procedure are related to the fact that the cornea is permanently and irreversibly damaged. A few of the problems reported are glare, overcorrection, cornea rupture and low vision. Photo-refractive keratectomy is the most recent procedure. This method uses an excimer laser to burn part of the exterior of the central cornea, and therefore flattens it in a more uniform manner than radial keratotomy. The damage to the cornea is reduced and the image quality is improved. This surgical procedure is still experimental, the long term consequences of burning the cornea are unknown and the procedure requires very costly and cumbersome electro-optical apparatus.

OBJECT AND SUMMARY OF THE INVENTION

The object of this invention is to provide an improved means to correct all refractive errors, myopia, hyperopia and astigmatism, with a simple device. The device is much easier to use than the prior art. In contrast to the prior art, this device alters the shape of the cornea by plastically deforming it under the force created by a vacuum. The cornea is not cut, burned or damaged. The cornea is stretched beyond its elastic range, therefore it is plastically deformed permanently.

An object of this invention is to deform the areas of the cornea that are placed under openings of a vacuum chamber. If the openings are elongated in a given direction, it is shown below that the stress created by the vacuum can deform those areas plastically in the perpendicular direction.

The device described by this invention stretches corneal tissue, called stroma, in a preferential direction or pattern, creating a permanent plastic deformation in that direction. When the vacuum chamber has radially elongated openings that are uniformly spaced, myopia can be corrected. When the vacuum chamber has circular or tangential openings, hyperopia can be corrected. When the openings are not uniformly spaced astigmatism can be corrected.

DETAILED DESCRIPTION OF THE INVENTION

Figure 1:
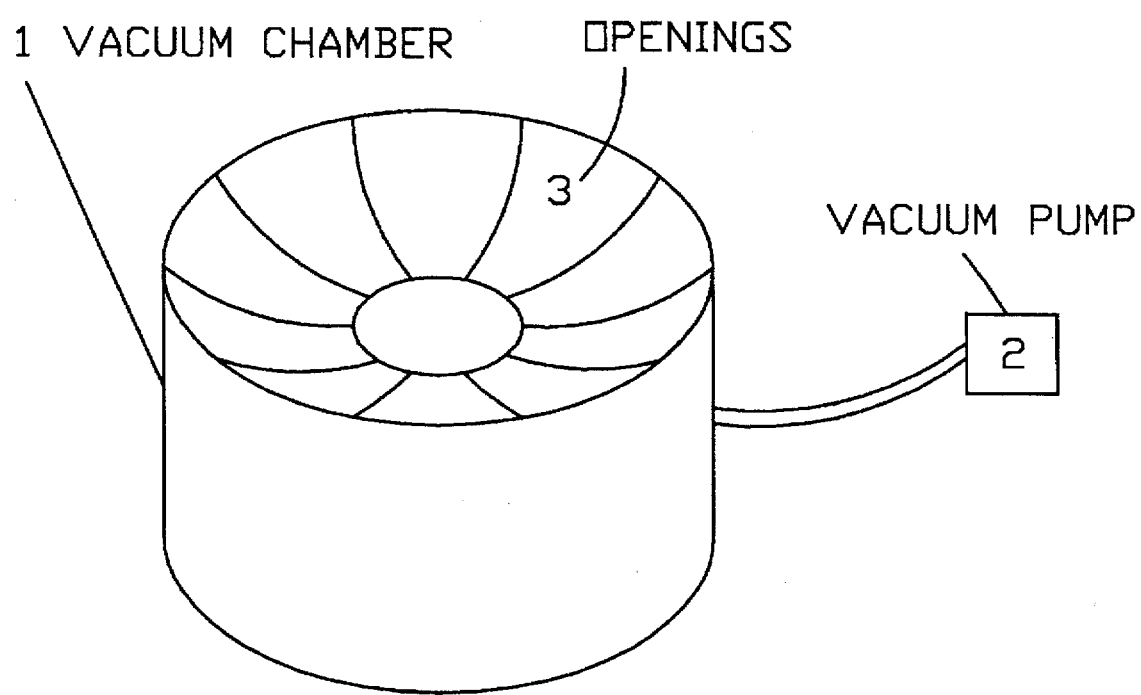
FIG. 1 shows a preferred embodiment of the invention for the correction of myopia. It depicts a vacuum chamber with ten openings in the form of elongated circular sectors.

The present invention is designed to correct refractive errors by altering the shape of the cornea of the eye by means of a force created by a vacuum. The method and means of the present invention is understood by reference to FIG. 1. In this arrangement a vacuum chamber 1 is connected to an ordinary vacuum pump 2 by some ordinary means, such as flexible tubing. The vacuum chamber 1 is open in the top, as depicted in FIG. 1, where several openings are present. There are ten interconnected openings in FIG. 1, they are marked with numeral 3. The exact number of openings is not important. The open side of the vacuum chamber is placed in contact with the cornea of the eye. To this end, this side of the vacuum chamber is shaped to approximately conform to the shape of the cornea. This side is therefore of a spherical or quasi-spherical shape with a radius of about 8 mm.

Figure 2:
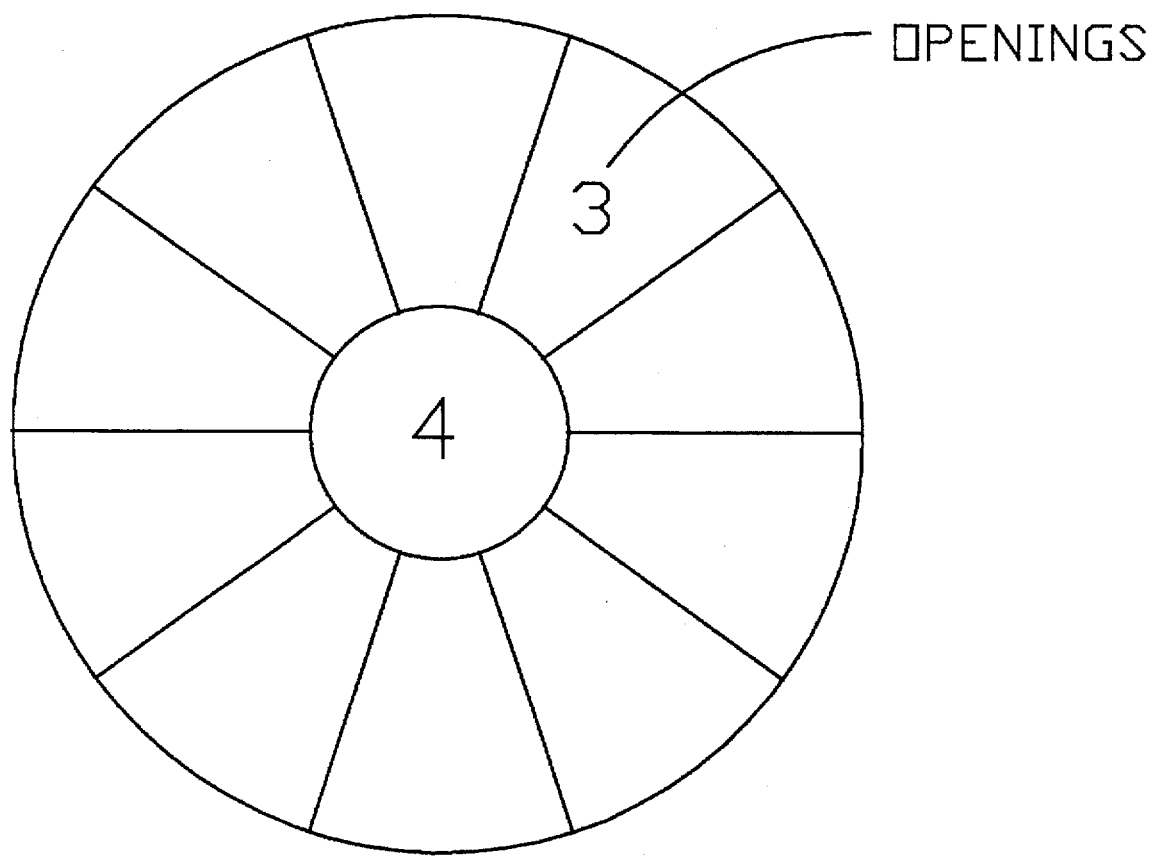
FIG. 2 shows a top view or projection of the openings of the vacuum chamber in FIG. 1.

FIG. 2 shows this side as a top view or projection. When placed on the cornea, the vacuum chamber 1 is fully closed by the surface of the cornea. A vacuum then created by vacuum pump 2 will create a negative pressure and suction force. This force will tend to distend the areas of the cornea covering the openings towards the vacuum chamber. The net pressure is the difference between the pressure (vacuum) created in the vacuum chamber by the vacuum pump and the atmospheric and intraocular pressure together. Since the atmospheric pressure is much greater than the intraocular pressure, the atmospheric pressure is substantially the maximum pressure that can be applied to the cornea with this device. All the openings apply the same pressure to the areas of the cornea that they cover because they are connected to the same vacuum pump by a common vacuum chamber. FIG. 2 shows in detail the openings 3 that are in contact with the cornea. They are in the form of circular sections, except that the central area of the chamber is in the form of a cylindrical hole or window 4, where no vacuum is applied. In this way, the central part of the cornea is not stretched. The force applied to the cornea at each opening by the vacuum tends to push those areas of the cornea toward the vacuum chamber. Those areas of the cornea in contact with the inside and outside circles and the connecting spokes are not pushed inward.

A vacuum of such pressure is applied to the chamber so that the cornea sections in contact with the openings deform beyond the elastic range, that is, there is a plastic deformation of a permanent nature. As it will be explained below, the deformation occurs in the direction perpendicular to the elongated direction of the opening. It is known, and it can be seen, that a permanent elongation of the cornea along circumferences centered in the center or apex of the cornea causes the cornea to flatten in the center. This is the desired result for the correction of myopia.

Figure 3:
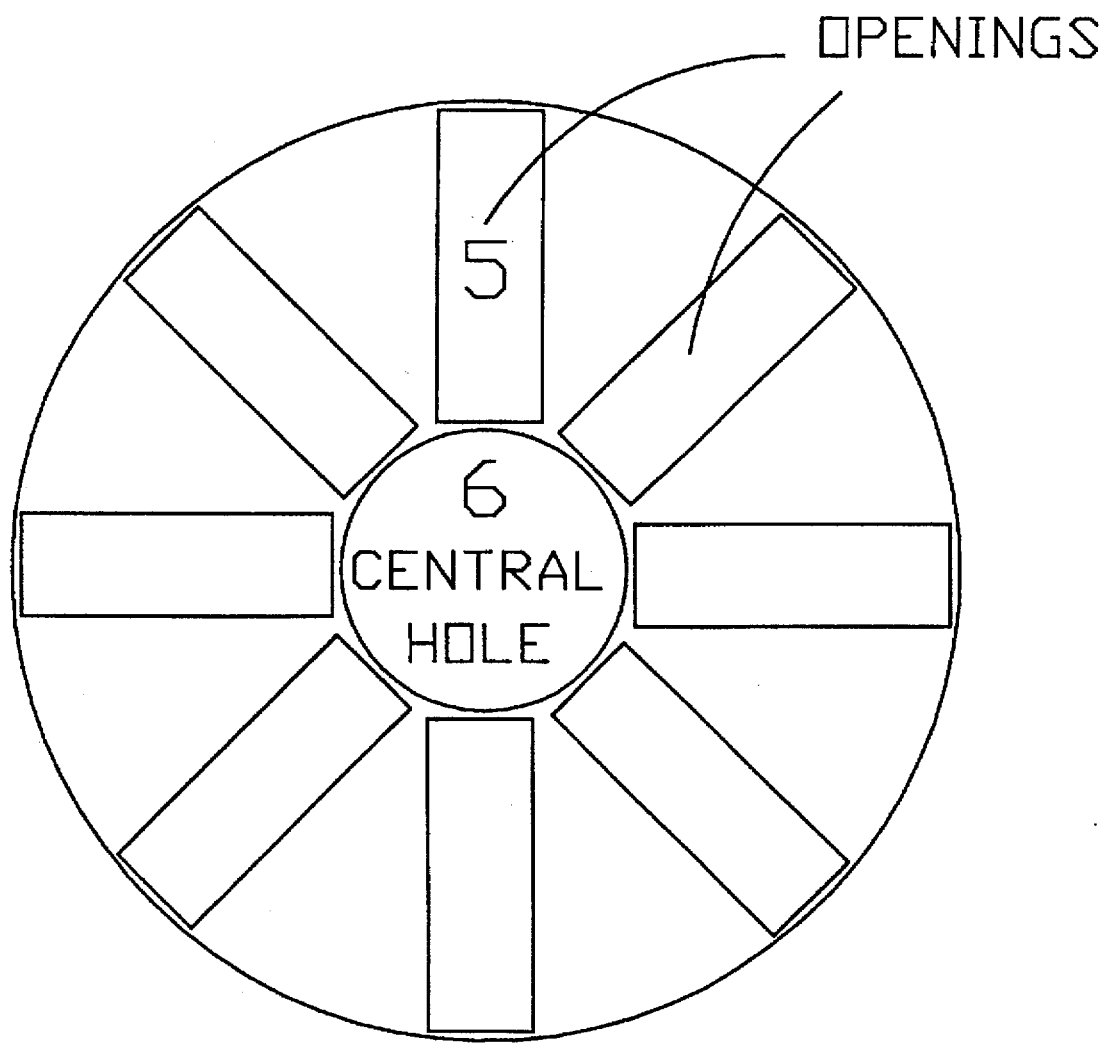
FIG. 3 shows a projection of alternative openings of the vacuum chamber in the form of eight radial rectangles for the correction of myopia.

FIG. 3 depicts a variation of the vacuum chamber that achieves the same result. Instead of openings in the form of circular sections, the openings 5 are rectangles. The form of the openings is not important, as long as they are elongated in the radial direction for the correction of myopia.

Figure 4:
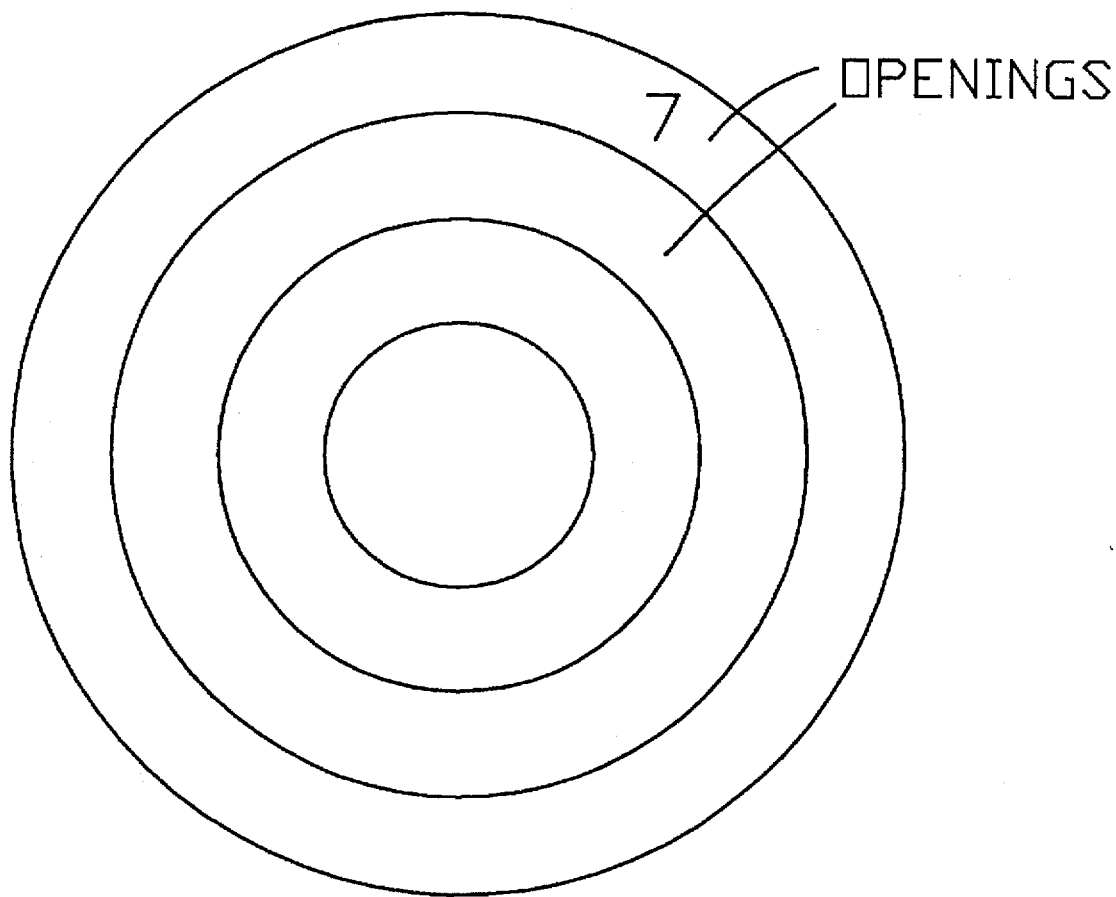
FIG. 4 shows a projection of alternative openings of the vacuum chamber in the form of three rings for the correction of hyperopia.
Figure 5:
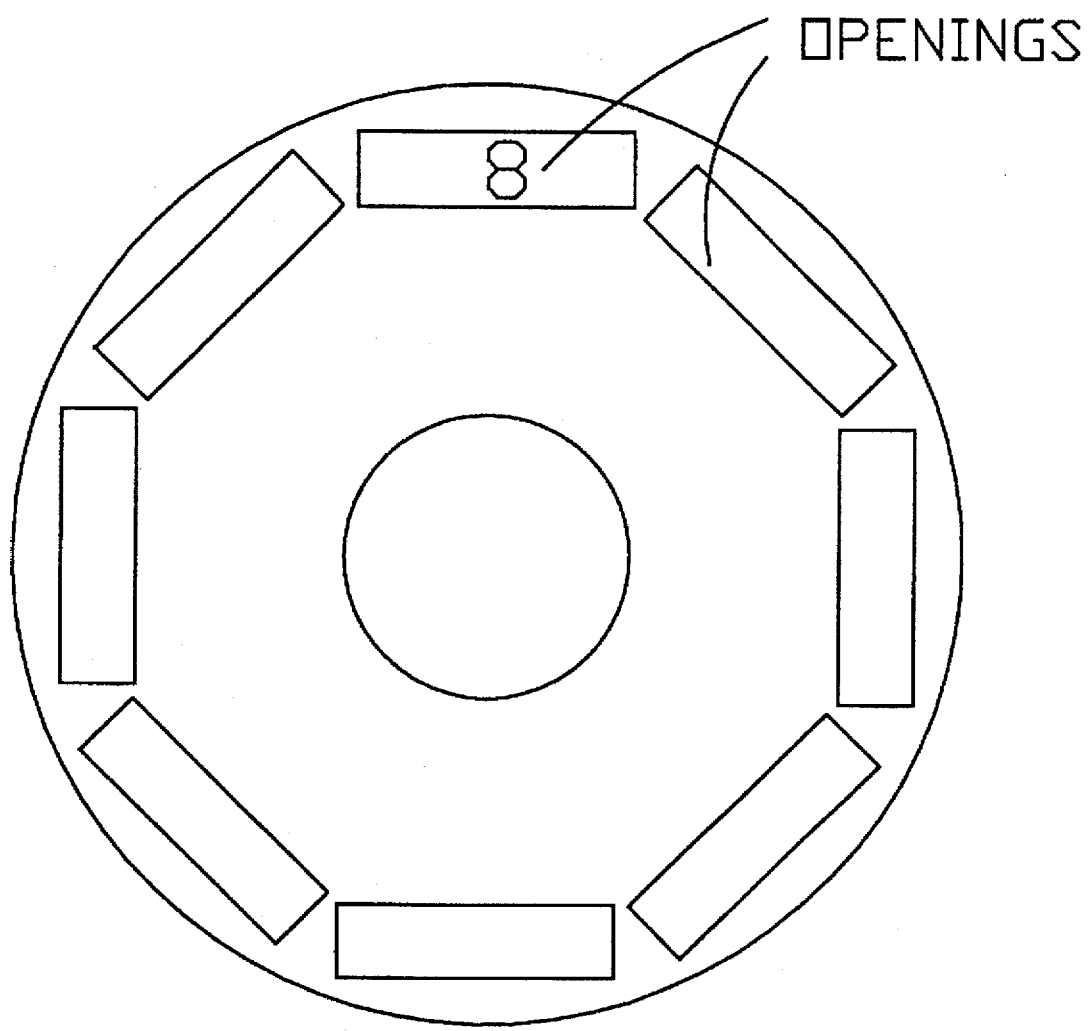
FIG. 5 shows a projection of alternative openings of the vacuum chamber in the form of eight tangential rectangles for the correction of hyperopia.

To correct hyperopia, openings such as those depicted in FIG. 4 and FIG. 5 should be used. FIG. 4 shows circular openings 7, while FIG. 5 shows tangential openings 8. In these configurations, the permanent deformation or stretch of the cornea occurs in the radial direction. It is known that such deformation causes the cornea to become steeper, that is, of a smaller radius of curvature. This is the desired effect to correct hyperopia.

FIGS. 3 to 5 depict the openings of the vacuum chamber as a top view or projection. As in FIG. 1, the three-dimensional shape of the openings is quasi spherical, so that it approximately conforms to the shape of the cornea.

FIGS. 1 to 5 depict all openings equally spaced around the meridians of the circumference. In this way the deformation of the cornea will be circumferentially uniform. This is the desired result for the correction of simple myopia and hyperopia. However, for the correction of astigmatism, where the eye has different refractive power across the meridians, the openings should be spaced unequally and in such a way as to compensate the eye irregularity.

Figure 6:
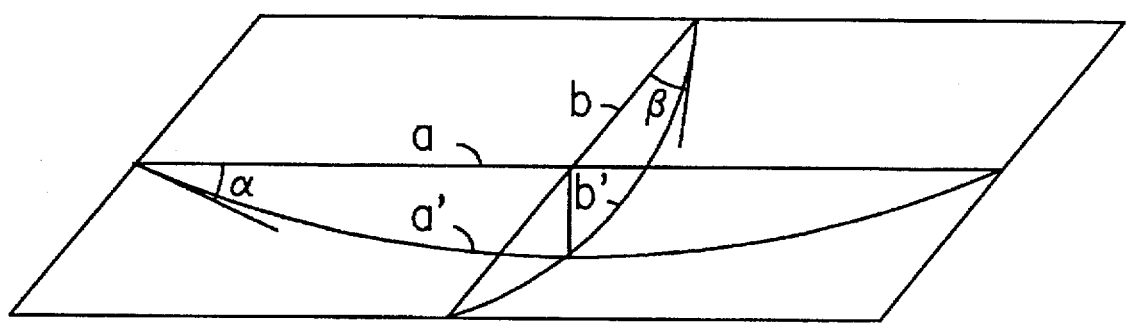
FIG. 6 illustrates how rectangular openings can produce a plastic deformation in one direction.

FIG. 6 depicts the deformation of the cornea placed in contact with the openings in FIGS. 3 and 5 when a vacuum is applied. Letters a and b depict the cross section of the cornea covered by the opening when no pressure is applied. Letters a' and b' depict the cross section of the cornea covered by the opening when pressure is applied. The same letters, a, b, a' and b' are used below to denote the dimensions of a, b, a' and b' respectively. It can be seen that the $\cos(\alpha)$ is approximately equal to a/a' and that $\cos(\beta)$ is approximately equal to b/b' where a and b are the dimensions of the rectangular opening, a' and b' are the dimensions of the stretched cornea, and $\alpha$ and $\beta$ are the angles that the cornea bends at the point of contact with the mid-points of the sides of the opening. Since a>b by definition of a rectangular or elongated opening, then $\alpha<\beta$. Since $\alpha<\beta$, then $\cos(\alpha)>\cos(\beta)$ or $(a'/a)<(b'/b)$. But a'/a and b'/b are the relative strain of the cornea in the two main directions of the rectangular opening. The strain in the direction of segment b is greater than in the direction of a. Therefore a vacuum can be applied that will strain the cornea to the point of plastic deformation in the direction of the short side of the rectangle, while there is no permanent deformation in the perpendicular direction. This analysis also applies to the opening in FIGS. 1, 2, and 4 because these openings, though they are not rectangular, are elongated or approximately rectangular.

Although elongated openings are preferred as the most effective way to alter the shape of the cornea, this invention is not limited to elongated openings. For example, circular openings that are arranged circumferentially, as in FIGS. 3 and 5, can produce a net flattening of the cornea. This is so because despite the fact that each opening produces the same stretch in all directions, the flattening caused by the circular stretch is greater than the steeping caused by the radial stretch.

What is claimed is:

1. A method for altering the shape of the cornea, comprising the steps of:

placing the openings of a vacuum chamber in contact with the surface of the cornea of the eye;

applying a vacuum to said vacuum chamber, said vacuum being of such pressure to exert a force towards said vacuum chamber on the portion of the cornea placed on said openings, said force causing stress and strain of said portion of the cornea, with said strain being beyond the elastic range of the cornea;

holding said vacuum for a length of time such that the cornea extends beyond its elastic range in said openings under the force exerted by said vacuum.

* * * * *